(12) United States Patent
Seki et al.

(10) Patent No.: US 6,916,623 B2
(45) Date of Patent: Jul. 12, 2005

(54) METHODS FOR PRODUCING PROTEIN DOMAINS AND ANALYZING THREE DIMENSIONAL STRUCTURES OF PROTEINS BY USING SAID DOMAINS

(75) Inventors: Eiko Seki, Kanagawa (JP); Takanori Kigawa, Kanagawa (JP); Shigeyuki Yokoyama, Kanagawa (JP)

(73) Assignee: Riken, Saitama (JP)

( * ) Notice: Subject to any disclaimer, the term of this patent is extended or adjusted under 35 U.S.C. 154(b) by 0 days.

(21) Appl. No.: 09/994,573

(22) Filed: Nov. 26, 2001

(65) Prior Publication Data

US 2002/0142387 A1 Oct. 3, 2002

(30) Foreign Application Priority Data

Mar. 6, 2001 (JP) ........................................ 2001-062703

(51) Int. Cl.$^7$ ............................................... G01N 33/53
(52) U.S. Cl. ............................ 435/7.1; 435/7.1; 435/6; 435/320.1; 435/68.1; 435/69.7; 530/350; 530/300; 536/23.1; 536/23.4
(58) Field of Search ........................ 435/7.1, 6, 320.1, 435/68.1, 69.7; 530/350, 300; 536/23.1, 23.4

(56) References Cited

FOREIGN PATENT DOCUMENTS

JP    A-2000-175695    12/1998

OTHER PUBLICATIONS

Chien et al., PNAS, vol. 88, pp. 9578–9582, 1991.*
Seki et al., 23rd Annual Meeting of the Molecular Biology Society of Japan Program and Abstract of Presentations, Nov. 25, 2000.*
Brenner et al. "Population Statistics of Protein Structures: Lessons from Structural Classifications" Current Opinion in Structural Biology 7:369–376 (1997).

Chothia et al. "Structural Repertoire of the Human $V_H$ Segments" J. Mol. Bio. 227:799–817 (1992).
Crameri et al. "Improved Green Fluorescent Protein by Molecular Evolution Using DNA Shuffling" Nature Biotechnology 14:315–319 (1996).
Ehrig et al. "Green–Fluorescent Protein Mutants with Altered Fluorescence Excitation Spectra" FEBS Letters 367:163–166 (1995).
Orengo et al. "The CATH Database Provides Insights Into Protein Structure/Function Relationships" Nucleic Acids Research 27(1):275–279 (1999).
Prasher et al. "Primary Structure of the *Aequorea victoria* Green–Fluorescent Protein" Gene 11:229–233 (1992).
Suen et al. "Molecular Cloning of the Mouse grb2 Gene: Differential Interaction of the Grb2 Adaptor Protein with Epidermal Growth Factor and Nerve Growth Factor Receptors" Molecular and Cellular Biology 13(9):5500–5512 (1993).
Waldo et al. "Rapid Protein–Folding Assay Using Green Fluorescent Protein" Nature Biotechnology 17:691–695 (1999).
Kawasaki and Inagaki, Biochemical and Biophysical Research Communications (2001) 280:842–844.

* cited by examiner

*Primary Examiner*—Jon Weber
*Assistant Examiner*—Hope A. Robinson
(74) *Attorney, Agent, or Firm*—Morrison & Foerster LLP

(57) ABSTRACT

There is provided a method for producing a soluble protein domain comprising: (a) preparing two or more DNA fragments by partially digesting a DNA coding for a protein; (b) expressing the protein which is coded on each of said DNA fragments, as a fusion protein with a functional protein; (c) selecting the fusion protein exhibiting said function among two or more fusion proteins synthesized in step (b); and, (d) synthesizing the soluble protein domain which is coded on said DNA fragment in a cell-free system, wherein said soluble protein domain is included in said fusion protein selected in step (c). By using this method, it can be easy and efficient to analyze the three dimensional structure of proteins of many clones.

18 Claims, 5 Drawing Sheets

METHODS FOR PRODUCING PROTEIN DOMAINS AND ANALYZING THREE DIMENSIONAL STRUCTURES OF PROTEINS BY USING SAID DOMAINS

RELATED APPLICATIONS

This application claims priority to Japanese Patent Application No. 2001-062703 filed on Mar. 6, 2001.

FIELD OF THE INVENTION

The present invention relates to a method for producing a soluble protein domain and for analyzing a three dimensional structure of a protein. More specifically, the present invention relates to a method for selecting a basic unit of protein which is called a "fold" or "domain," followed by synthesis of said selected protein domain using cell-free systems, to a protein domain synthesized by this method, and to a method for analyzing the three dimensional structure of proteins by using said protein domain.

BACKGROUND OF THE INVENTION

Recently, DNA sequences of various species have been determined rapidly, and "structural genomics" is recognized as an important research area. With respect to a large number of genes selected from a mass of information about genomic sequences, structural genomics aims the systematic determination of three dimensional structures of proteins coded on each gene, as well as the comprehensive study of structure function relationships.

In the research of structural genomics, many types of proteins ranging from 30,000 to more than 40,000 in case of human's proteins, can be targets of the structural analysis. However, it is thought that the three dimensional structures of proteins encoded on the human genome consists of one or several thousand folds or domain units, and that the combination of these protein folds and domains represents the variation of protein functions (Chothia, C., et al, J.Mol.bio., 227, 799–817. (1992); Brenner, S. E., Chothia, C., Hubbard, T. J., Curr.Opin.Struct.Biol., 7, 369–376. (1997)).

In the existing methods of protein synthesis, genetic engineering methods in which full length genes cloned from cDNA or a genomic library are introduced into living cells such as E. coli have been widely used, however, it is difficult to obtain proteins which are toxic to host cells and/or degrade easily because of instability. It is also difficult to obtain proteins which aggregate easily in host cells as soluble proteins.

In eukaryotes such as human cells, most proteins are multiple complexes of relatively small functional domains, as the result of evolution by gene duplications (Orego, C. A., et al., Nucleic Acids Res., 27, 275–279. (1999)). Particularly, membrane-bound proteins and the like have partial sequences that are rich in hydrophobic amino acids which bind to cell membranes. In the case where these proteins are expressed in an intact form in heterogeneous cells, they are likely to be insoluble, and it is difficult to maintain their intact three dimensional structures and functions in vivo.

Then, experiments have been performed to prevent formation of incorrect three dimensional structures and generation of insoluble aggregates when heterogenes are overexpressed in microorganisms such as recombinant E. coli. These experiments have been focused on expressing proteins from heterogenes or from heterogenes fused with genes expressing soluble proteins. These proteins may be expressed in presence of a chaperone protein, which promotes the formation of three dimensional structures, at a low temperature or under specific medium conditions. However, in the case of particular genes, the soluble protein products cannot be obtained by any of these methods.

To solve this problem, it has been reported that green fluorescent protein (GFP) works as a "folding reporter", when the protein of interest is fused to the N-terminal of GFP (Waldo, G. S., Standish, B. M., Berendzen, J., Terwilliger, T. C., Nature Biotechnology 17, 691–695. (1999)). In this research, the consequent formation of the GFP chromophore is directly related to the proper folding of the fused upstream protein, and through GFP fluorescence, the protein folding of the fused protein could be identified. According to this report, the functional formations of three dimensional structures of the proteins ligated to the upper region of GFP can be predicted only by measurements of fluorescence strengths of the recombinant E. coli, without any measurement of functions themselves of the proteins ligated to the terminus of GFP. Using the results as indices, mutants with rates of folding are higher than that of the wild type can be made, and mechanisms of formation of the three dimensional structure can be studied.

In general, these specialized approaches geared toward evaluating individual proteins have not been sufficient as methods for high-throughput analyses of three dimensional structures of many proteins, as well as for systematic understandings of structures and functions of the proteins.

SUMMARY OF THE DISCLOSURE

It is an object of the present invention to provide a rapid and easy method to select highly soluble protein domains suitable for three dimensional structural analysis.

It is a further object of the present invention to provide a method to analyze the three dimensional structures of proteins using soluble protein domains selected in this way.

In order to solve the problems described above, the present inventors focused on the domain structures of proteins. The inventors hypothesized that, even if the whole protein is insoluble, the individually expressed partial structures constituting the domains might be soluble. On the basis of this hypothesis, many DNAs contained in a DNA library were fragmented simultaneously, and ligated to a gene of a functional protein to express fusion proteins. A very good correlation resulted between the function of the fusion protein with the functional protein and the solubility of partial structures of proteins coded on the fragmented DNAs. It has been found that, using this correlation as an index, protein domains expected to be suitable for the analysis of three dimensional structure can be selected efficiently from tens of thousands of clones. These findings have led to the following inventions.

According to a first aspect of the present invention, there is provided a method for producing a soluble protein domain comprising:

(a) preparing two or more DNA fragments by partially digesting a DNA coding for a protein, (b) expressing the protein which is coded on each of said DNA fragments as a fusion protein with a functional protein, (c) selecting the fusion protein exhibiting said function among two or more fusion proteins expressed in step (b), and (d) synthesizing the soluble protein domain which is coded on said DNA fragment in a cell-free system, wherein said soluble protein domain is included in said fusion protein selected in step (c).

In a preferred embodiment of the present invention, said DNA fragments in step (a) are prepared by partially digesting the expression vector comprising said DNA coding for said protein and a gene for a functional protein, with a DNA decomposing enzyme.

In another preferred embodiment of the present invention, said functional protein in step (b) is any one selected from the group consisting of an enzyme, a binding protein, a luminescent protein and a fluorescent protein. A portion thereof having said function is also included in the present invention. In a further preferred embodiment, said fluorescent protein is a green fluorescent protein or a derivative thereof.

In another preferred embodiment of the present invention, said selection in step (c) is performed by transforming a recipient cell with the expression vector comprising each of said DNA fragments and the gene of said functional protein, and selecting the clone which exhibits said function in the obtained transformants. *E. coli* cell can be used as said recipient cell.

In a still further preferred embodiment of the present invention, two or more fusion proteins are synthesized in cell-free system, and said selection in step (c) is performed by measuring said function of the expressed proteins.

According to the second aspect of the present invention, there is provided a soluble protein domain synthesized by the method as described above.

According to the third aspect of the present invention, there is provided a method for analyzing the three dimensional structure of a protein comprising:

synthesizing the soluble protein domain by the method comprising the following steps:
(a) preparing two or more DNA fragments by partially digesting a DNA coding for a protein,
(b) expressing the protein which is coded on each of said DNA fragments, as a fusion protein with a functional protein,
(c) selecting the fusion protein exhibiting said function among two or more fusion proteins expressed in step (b),
(d) synthesizing the soluble protein domain which is coded on said DNA fragment in a cell-free system, wherein said soluble protein domain is included in said fusion protein selected in step (c); and
analyzing the three dimensional structure of said soluble protein domain by X-ray crystallography or NMR spectroscopy.

DETAILED DESCRIPTION OF THE INVENTION

Figure 1:
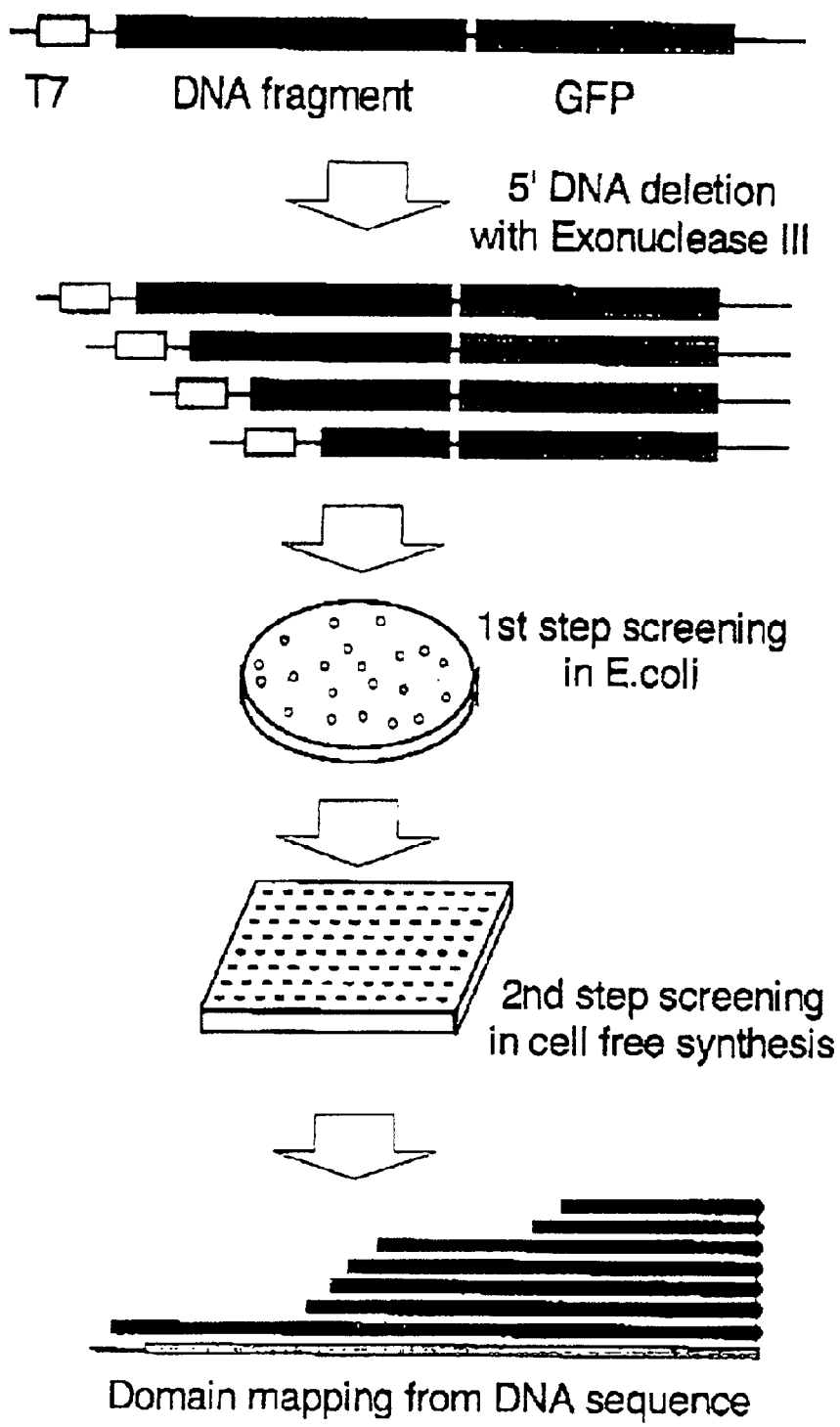
FIG. 1 shows a schematic diagram showing an embodiment of the present invention.

Preferred embodiments of the present invention are explained in detail by reference to figures as follows. FIG. 1 is a schematic diagram showing an embodiment of the present invention.
(A) Fragmentation of DNA.

Any DNA coding for proteins or having the possibility to code for proteins can be used for the method of the present invention. Any clone selected from cDNA libraries or genomic DNA libraries can be used for this purpose. DNA derived from single clone or a mixture of plural DNA clones can be used. Particularly, it is preferable to use full length cDNA coding for whole proteins from the N-terminus to the C-terminus.

As a method for partial digestion of said DNA, for example, a physical digestion method such as ultrasonic or a chemical digestion method such as DNA decomposing-enzyme treatment may be used. As a DNA-decomposing enzyme, DNase I, various Restriction enzymes, Bal31, Exonuclease III, and other generally known enzymes can be used. In the present invention, it is preferable that full length cDNA is digested to produce various length of DNA fragments uniformly. Methods wherein the DNA can be digested from the terminus by single strand DNA-decomposing enzymes such as Exonuclease III to produce various sizes of DNA fragments may be used. Furthermore, it is essential that the digested DNA fragments are properly ligated to a gene coding for a functional protein.

There are several methods to fragment DNA and construct a DNA library of various lengths. We can classify them in two typical methods, out-vector fragmentation and in-vector fragmentation. In the out-vector fragmentation method, various lengths of DNA fragments are made at first, and then the fragments are cloned into an expression vector. In the in-vector fragmentation method, the DNA previously cloned into an expression vector is deleted from the fixed places in the vector to make various lengths of DNA fragments. With regard to the methods of the present invention, both of the above methods can be used, however, the method of in-vector fragmentation is more preferable. When a target DNA is randomly fragmented out of vector, deleted fragments should be re-ligated to the expression vector. This re-ligation leads the library to incline toward shorter fragments, for small fragments tend to be easily ligated. The ligation efficiency of blunt-end fragments is low compared to in-vector self-ligation. Because there is no definite method for random fragments with blunt ends to be ligated in the selected direction the number of effective fragments in the library, ligated in the right direction to a functional protein, automatically decreases to half. On the other hand, when DNA is fragmented in vector, the homogeneity of the deletion library is ensured, and self-ligations make it possible to efficiently make correctly ligated clones.

(B) Expression of Fusion Proteins with Functional Proteins.

Proteins coded on the DNA fragments described above are expressed as fusion proteins with functional proteins. In the present invention, functional protein means the protein which expresses specific catalytic activities like enzymes and specific binding activities to specific materials like antibodies. Using these functions as indices, solubility of proteins coded on the DNA fragments can be predicted. As a concrete example, they can be prepared using the reporter genes mentioned below.

For example, a β-Galactosidase gene derived from *E. coli* (lac Z) has been used frequently as a reporter gene for transformation of various cells. A substrate for this enzyme in vivo is lactose, but almost all β-galactosides can be hydrolyzed by this enzyme. For example, the colorless substrate, o-nitrophenyl β-D-galactopyranoside (ONPG), is hydrolyzed to generate yellow o-nitrophenol which absorbs light at 420 nm. And, x-gal (5-bromo-4-chloro-3 indolyl β-D-galactopyranoside) is degraded by this enzyme to show a color reaction of indigo blue.

Alkaline phosphatases are suitable for highly sensitive measurements because the molecular catalytic activity of the enzyme extremely high, and various fluorescent or luminescent substrate for the enzyme have been developed.

Firefly luciferase catalyzes oxidation of luciferin in the presence of ATP to catalyze the chemiluminescence reaction generating photons. Usually, a sharp spike-wave light is radiated, followed by rapid decay. However, in the case where Coenzyme A is added to the reaction system, more uniformly photoradiation can be obtained.

In the present invention, it is especially preferable to use Green fluorescent protein (GFP). GFP is a fluorescent protein isolated from the Pacific jellyfish, *Aequorea victoria* and the like. Its role is to transduce, by energy transfer, the blue chemiluminescence of another protein, aequorin which is a luminescent protein co-localized with GFP, into green fluorescent light (Prasher, D., et al., Gene 11, 229–233. (1992)). In contrast to said aequorin and luciferase, GFP does not require the specific fluorophore, and forms a fluorophore (chromophore) automatically on its own apoprotein. For this reason, to use as indices of gene expressions, GFP has been expressed in bacteria, yeast, slime mold, plants, insects, and in mammalian cells using the cloned GFP cDNA. Furthermore, mutations have been introduced into the GFP gene by various methods to make various GFP variants. It has been reported that, among the variants, some show stronger fluorescent intensities than the wild type GFP, and others which radiate fluorescence at the different wave lengths (Ehrig, T., O'kane, D., and Prendergast, F. FEBS Lett., 367, 163–166. (1995); Crameri, A., Whitehom, E., Tate, E., and Stemmer, W., Nature Biotech., 14, 315–319. (1996)). In this invention, these GFPs or the variants can be used as a functional protein to construct rapid and easy screening systems.

Expression vectors of these fusion proteins are made by ligation between said DNA fragments and genes for functional proteins. Both eukaryotic and prokaryotic cells can be used as the expression system, and *E. coli* expression systems are preferably used. As an expression system of *E. coli*, any generally known system can be used. For example, a system in which expression is regulated by the promoter of T7 RNA polymerase/lactose operator, and the genes are introduced into host *E. coli* cells which express T7 RNA polymerase can be used.

(C) Selection of Clones Expressing Fusion Proteins with Functional Proteins.

Clones having the functions of said functional proteins are selected from transformants obtained by transformations of recipient cells with said expression vectors containing various lengths of DNA fragments. Proper selection methods are used in accordance with functions of the concerned functional proteins. For example, enzymes and binding proteins can be detected by detections of the catalytic activities and the binding activities to the ligands, respectively. In the case of GFP used under the preferable condition of this invention, the fluorescent intensities can be measured with basic spectrofluorometers by suspending said transformant cells in proper buffer solutions.

Alternatively, without or after the transformation of said recipient cell, said functions can be also measured by expressing the fusion proteins in cell-free systems.

According to the present invention, there is an extremely good correlation between said functions of fusion proteins with functional proteins detected in this manner and the solubility of the fusion proteins with functional proteins. As shown in the following examples in detail, this can be clearly understood from the embodiments of the present invention. Furthermore, it has been indicated that, in the case where proteins which are fused into the functional proteins consist of the plural domains, there is a close correlation between solubility of proteins obtained by fragmentation of the proteins and the domain structures.

Therefore, it is suggested that, among the clones selected by the methods of the present invention, there is a good possibility that the protein fragments fused into the functional proteins may form independent domains in the original intact proteins.

(D) Expression through Cell-Free Systems.

Domains of proteins selected in this manner can be synthesized efficiently through cell-free systems. In cell-free systems, because PCR products can be used directly as templates for expressions, simultaneous treatments of multiple samples and additions of various expression tags can be easily done.

As for this invention, said cell-free systems are in vitro protein synthesis systems using cell extract. As the cell extract, a eukaryotic or prokaryotic cell extract containing factors required for protein synthesis such as ribosome, tRNA, and so forth can be used. As the eukaryotic or prokaryotic cell, any of the generally known cells can be used. As concrete examples, *E. coli*, thermophilic bacteria, wheat germ, rabbit reticulocyte, murine L-cell, Ehrlich ascitic cancer cell, HeLa cell, CHO cell, and budding yeast can be enumerated. Especially, *E. coli* cell extract (for example, *E. coli* S30 cell extract fraction) or wheat germ cell extract is desirable for the high yield. And, to raise productivity of the cell-free systems, a synthesis system using the improved dialysis method (see JP Patent Kokai Publication JP-A-2000-175695) can also be used.

(E) Domains of Soluble Proteins.

The protein domains are supposed to be soluble when they are properly folded during protein synthesis. Proteins consist of combinations of several domains, and each domain reacts as a functional unit. Therefore, the synthesized domains of soluble proteins present practical utility value to analyze in vivo functions and to search for inhibitors of those proteins and the like.

(F) Analysis of the Three Dimensional Structure of Protein.

In this invention, the synthesized soluble domains of proteins can be used for three dimensional structural analyses. Analysis of the three dimensional structure of protein domains can be achieved through various methods, although it is preferable to use X-ray crystallography or NMR spectroscopy. Furthermore, because the method of this invention provides the correct folding, protein solutions of high solubility can be prepared. Therefore, this method is thought to be suitable especially for NMR spectroscopy. For three dimensional structural determinations of protein domains through NMR, multi-nuclear, multidimensional NMR spectra such as HNCA spectra can be measured using the $^{13}C/^{15}N$ labeled samples, or by using a combination of the $^{13}C/^{15}N$ labeling and stable isotopic labeling such that the methylene groups of amino acids are specifically deuterated. Moreover, because NMR can be used for various research such as research in intermolecular interactions and those in biomolecular dynamics of proteins, nucleic acids, among others, this method can also be used for research of the functions of target proteins.

EXAMPLES

The present invention is explained in more detail by reference to the following examples using Grb2 which is a mammalian growth factor receptor protein. Grb2 is one of the most extensively studied adaptor proteins, and is a key element in the signal transduction pathway. However, the present invention is not limited to the following examples.

Example 1

Construction of Plasmids and Introduction of Mutations pGFPuv (Clontech), used as the reporter gene, was mutated at three sites using a site-directed mutagenesis kit (Stratagene). Replacement of phenylalanine at the 64$^{th}$ residue to leucine (F64L) and serine at the 65$^{th}$ residue to threonine (S65T) are the mutations to obtain red-shifted excitation peak and fluorescence about 35 times more intensely than wild type GFP when excited at 488 nm. These mutations also display improved solubility and the more efficient folding of proteins (Cormack, B. P., Valdivia, R. H., Falkow, S., Gene 173, 33–38. (1996)). The other mutation is a silent mutation to terminate the NdeI restriction site.

Figure 2:
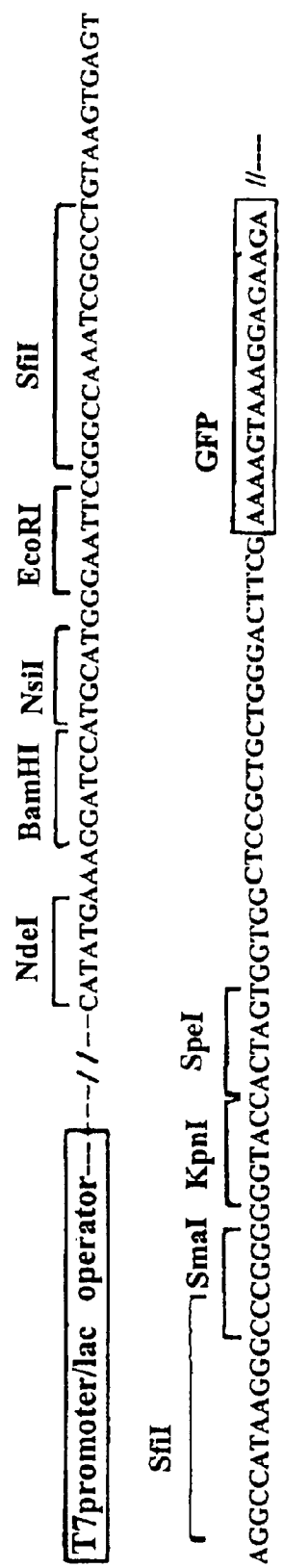
FIG. 2 shows the structure in the vicinity of a multicloning site of the plasmid vector (SEQ ID NO:1), pGFPsfiI, for expression of fusion proteins with GFP.

To produce GFP-fusion proteins ligated to the C-terminus of proteins coded on the inserted DNA, an expression vector has been constructed comprising a T7 promoter, the DNA insertion site, the mutant GFP gene, and a T7 terminator sequence. One plasmid constructed in this way, pGFPsfiI, has a replication origin and an ampicillin resistant gene derived from a plasmid, pET17b (Novagen), and is ligated to said GFP gene through chemically synthesized multi-cloning site (MCS) downstream of a NdeI restriction site of the T7 promoter/lac operator. The structure in the vicinity of this MCS is shown in FIG. 2 (as also listed in SEQ ID NO:1).

Example 2

Construction of Deletion Library

Grb2 cDNA (without stop codon) was ligated to the SfiI site of the plasmid pGFPsfiI in the correct direction and frame to C-terminal GFP. Then, after digesting the N-terminal side of the inserted DNA with EcoRI or a NsiI, the inserted DNA was deleted with Exonuclease III from the 5' end, the region of single stranded DNA was digested with Mung-bean nuclease. Finally, the blunt ends were made using DNA polymerase, Klenow fragment. The lengths of deleted DNA were selected by electrophoresis and the size selected DNA was self-ligated for transformation of E. coli JM109(DE3) strain (Promega) to prepare the deletion library containing Grb2 cDNA.

Example 3

Protein Expression

For the first screening step, the deletion library of GFP-fusion vectors prepared in Example 2 was transformed in JM109(DE3) (Promega) and cultured at 37° C. over night. The fluorescence of the derived colonies was observed by excitation with a Dark Reader (BM Science) at 420–500 nm. When roughly observed with the excitation of the blue light (420–500nm), the obtained colonies could be classified into 3 categories on the basis of fluorescent intensity: strong, medium, and none. Among them, each 8 colonies of those emitting strong fluorescence, those emitting medium fluorescence, and those emitting no fluorescence were selected. And, base sequences of the total 24 clones were determined to identify the deletion sites. Most of the clones emitting strong fluorescence had relatively short (shorter than 35 amino acid residues) protein fragments of Grb2. This result suggests that the folding properness of the short protein fragment, with several tens of amino acid residues, is not affected by the fused GFP fluorescence. Furthermore, it was found that the fluorescent intensity of the obtained colonies depended not only on the solubility of the expressed GFP-fusion proteins, but also the growth of E. coli. Thus, to analyze the accurate fluorescence intensity of the GFP-fusion protein without influence of the E. coli growth, the cell-free protein synthesis system was used for further analysis.

Figure 3:
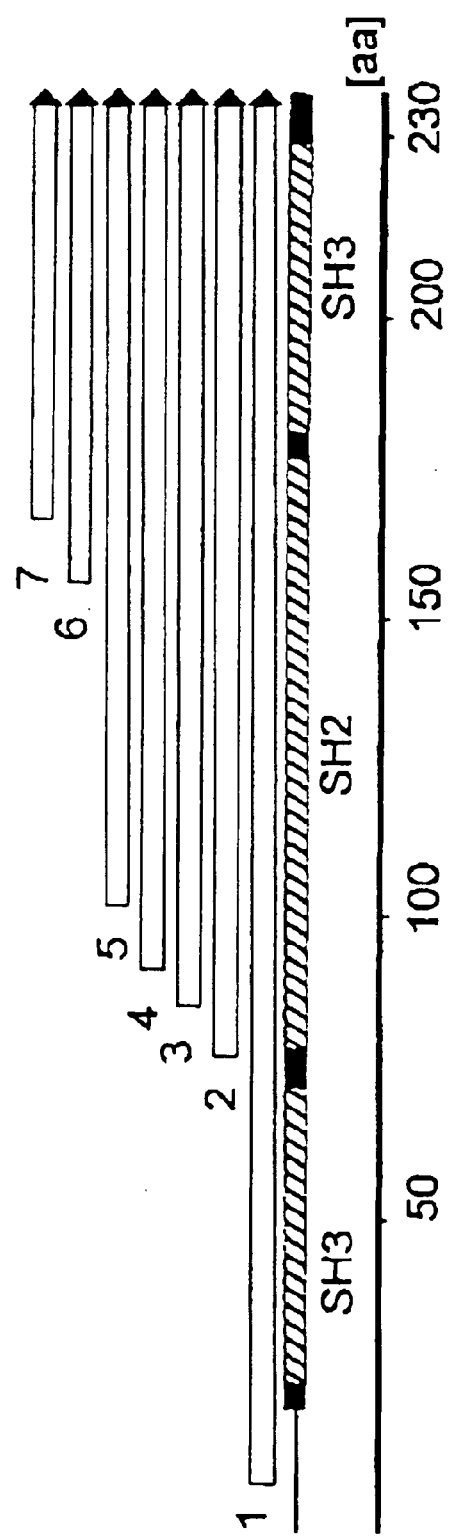
FIG. 3 shows the deletion sites of Grb2 protein coded on fragmented DNA.

For the second screening step, from among 24 colonies selected in the first screening step described above which contained deleted Grb2 longer than 40 amino acid residues, 7 clones were selected and E. coli cell-free protein synthesis was carried out for 1 hour at 37° C. Template DNAs for the cell-free system were amplified by PCR. Fluorescence was measured with 96 well type fluorometer Arvo (Wallac Berthold)(excitation 485 nm, emission 535 nm). FIG. 3 shows the lengths of Grb2 genes carried by the 7 clones, and the result of determinations of the nucleotide sequences with full length Grb2 cDNA (Suen, K., Bustelo, X. R., Pawson, T., Barbacid, M., Mol.Cell.Bio., 13, 5500–5512. (1993)). Deleted fragments of the protein are indicated by arrows. The full length Grb2 cDNA is indicated by a bar with the SH3, SH2, and SH3 domain regions speculated from the amino acid sequence homologies. Number under the horizontal axis is number of residues counted from amino terminus of the Grb2 protein. These 7 clones were synthesized as both the GFP-fusion and the intact forms (Grb2 fragments only), by the E. coli cell-free system.

Example 4

Correlation between Fluorescent Intensities of GFP and Solubility of Proteins The GFP-fusion proteins synthesized in E. coli cell-free system were centrifuged for separating into soluble and insoluble fractions. The intact proteins coded on the fragmented DNA were synthesized with $^{14}$C-labeled leucine ($^{14}$C-Leucine, Roche), detected by scintillation counter, analyzed by SDS-PAGE, and scanned by BAS2000 (Fuji Photo Film Co. Ltd. Japan). The GFP-fusion proteins were detected by Western blotting using anti-GFP antibody and CDP star (Roche) through MacBAS (Fuji Photo Film Co. Ltd. Japan).

Figure 4:
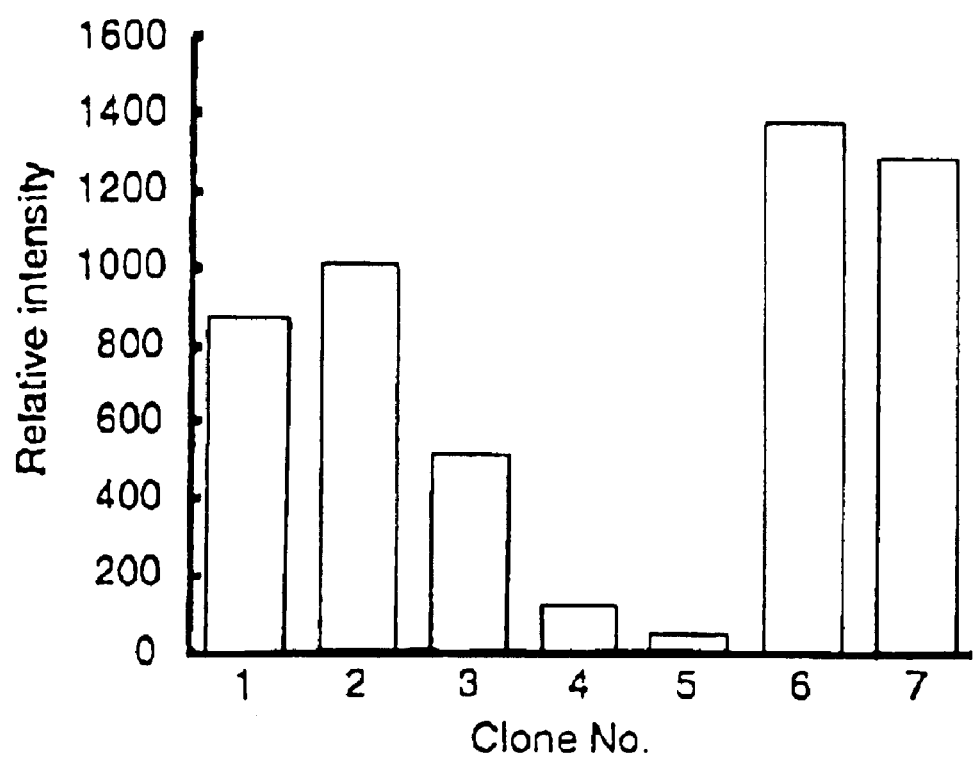
FIG. 4 shows fluorescent intensities of deletion Grb2-GFP-fusion proteins expressed in a cell-free system.
Figure 5:
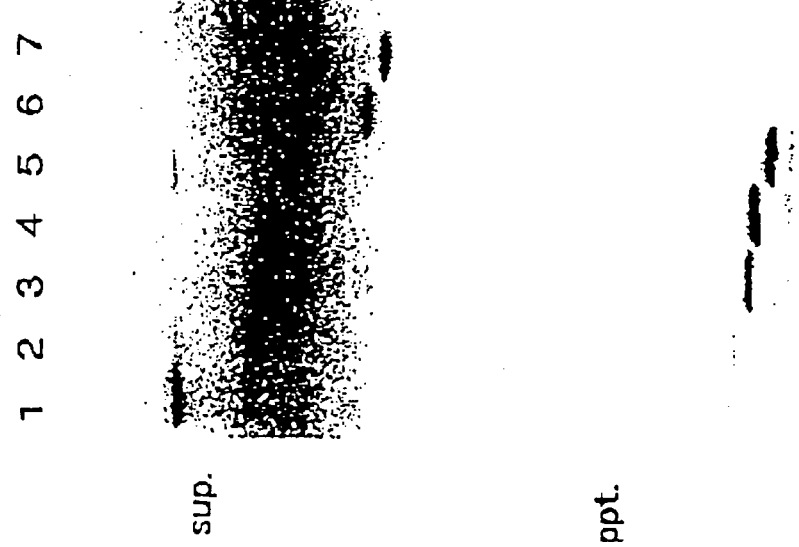
FIG. 5 shows the solubility of deletion Grb2 proteins expressed in a cell-free system. (a) solubility of intact deleted Grb2 synthesized with $^{14}$C-labeled Leucine and detected by scintillation counter. (b) Solubility of GFP-fused deleted Grb2, scanned with MacBAS after western blotting with anti-GFP antibody. All soluble fractions are shown in black bars, and insoluble fractions are shown in hatched bars. (c) SDS-PAGE of intact deleted Grb2 synthesized by cell-free system with $^{14}$C-labeled Leucine, scanned with BAS2000.
Figure 5:
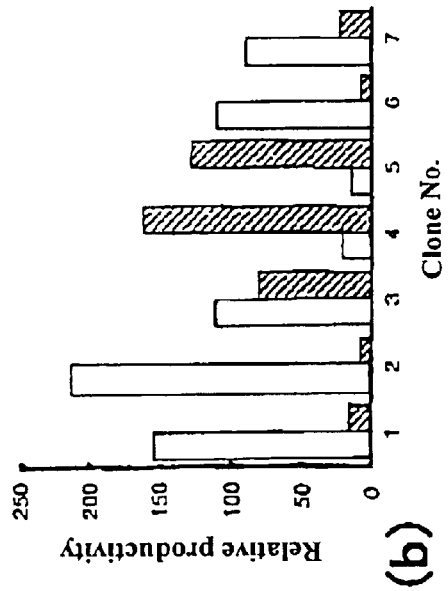
Figure 5:
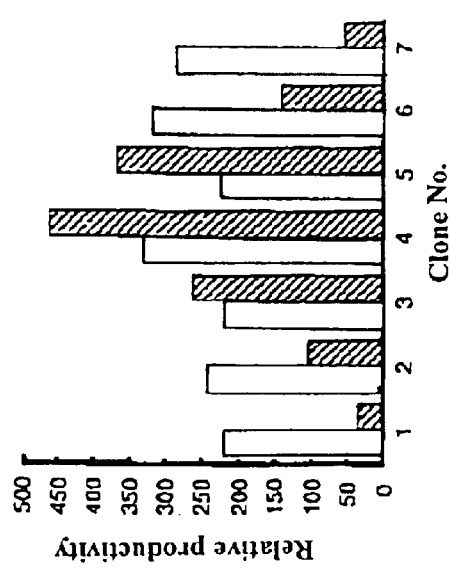

The fluorescence intensities, of said 7 GFP-fusion proteins expressed in E. coli cell-free system, were measured by fluorometer, and the results are shown in FIG. 4. And, the solubility of intact Grb2 coded on the fragmented DNA are shown in FIGS. 5(a) and (c). FIG. 5(a) is the result that the solubility of intact Grb2s coded on the fragmented DNA was measured by radioisotope labeling. FIG. 5(c) is the result that the same radioisotope labeled intact Grb2s were analyzed by SDS-PAGE. From these results, it was found that the fluorescence intensities were actually different with each other, and the difference was precisely linked to the intact fragment solubility. This result indicates that, by using the cell-free system, we obtained the ability to screen clones with more accuracy, reflecting the actual solubility of the fused proteins.

The solubility of GFP-fused form of these deleted Grb2 was also examined by Western blotting with the anti-GFP antibody (FIG. 5(b)). The amount of the GFP-fused protein within the insoluble fraction was closely linked to both the GFP fluorescence of the GFP-fused protein and the solubility of the intact fragment. On the other hand, interestingly, the amount of the GFP-fused protein within the soluble fraction was not linked to them. These data suggest that not all the GFP-fused proteins within the soluble fraction are properly folded to form the GFP chromophore, and GFP fluorescence is actually a good parameter that directly indicates the folding properness of the proteins.

Comparison Between Fluorescent Intensity and Grb2 Structure.

The correlation between the fluorescence intensity of GFP-fusion proteins with the fragmented Grb2 and the structure of full-length Grb2 was examined. As speculated from the amino acid sequence homologies, Grb2 protein consists of a single Src homology domain 2 (SH2) and two flanking Src homology domain 3 (SH3)(Suen, et al.). Comparison of the deletion sites of the 7 clones selected in Example 3 (FIG. 3) with the fluorescence intensities (FIG. 4) and the solubility (FIG. 5) of the GFP-fusion proteins measured in Example 4 reveals that said domain structures speculated from amino acid sequence homologies and the boundaries of the domain determined by the three dimensional structure of Grb2 have a close correlation with the fluorescent intensities and the solubility of these fusion proteins.

That is, if the N-terminal position of the deletion variant is at the boundary of the structural domain (clones 1, 2, 6, and 7), it is soluble and the fluorescence of the GFP-fusion becomes strong. If the N-terminal is within the structural domains (clones 4 and 5), it precipitates and the fluorescence is weak. In addition, the GFP-fusion protein of clone 3, which is slightly deleted into the SH2 domain and slightly precipitates, is weak but not totally abolished when compared with totally precipitating fragments (clones 4 or 5). Thus, using N-terminal deleted Grb2 variants, we successfully demonstrated the domain boundaries by GFP fluorescence.

The meritorious effects of the present invention are summarized as follows.

According to the present invention, soluble protein domains suitable for the analysis of the three dimensional structures of proteins can be expressed. Because they are expressed in a cell-free system, PCR products can be used directly as templates for expressions of the proteins, simultaneous treatments of many samples are easy, and various expression tags can be easily added. Therefore, by using the method of the present invention, the three dimensional structure of proteins of many clones could be analyzed easily with high efficiency compared to the ordinary methods.

It should be noted that other objects, features and aspects of the present invention will become apparent in the entire disclosure and modifications may be done without departing the gist and scope of the present invention as disclosed herein and claimed as appended herewith.

Also it should be noted that any combination of the disclosed and/or claimed elements, matters and/or items may fall under the modifications aforementioned.

What is claimed is:

1. A method for producing a soluble protein domain comprising:
   (a) expressing at least two nucleotide sequences each encoding a fusion protein comprised of different fragments of a starting protein and a protein exhibiting a function,
   (b) identifying a fusion protein exhibiting said function from among the proteins produced in step (a), so as to identify said fusion protein as comprising a fragment of said starting protein that is a soluble domain,
   (c) synthesizing the soluble domain that is included in the fusion protein identified in step (b) in a cell-free system; and
   (d) recovering the synthesized soluble domain synthesized in step (c).

2. The method of claim 1, wherein said protein exhibiting a function in step (a) is selected from the group consisting of an enzyme, a binding protein, a luminescent protein and a fluorescent protein.

3. The method of claim 2, wherein said fluorescent protein is a green fluorescent protein (GFP) or a GFP variant.

4. The method of claim 1, wherein said identifying in step (b) is performed in cells containing said nucleotide sequences by selecting a clone of said cells which exhibits said function.

5. The method of claim 4, wherein said cells are *Escherichia coil* (*E. coli*).

6. The method of claim 1, wherein the nucleotide sequences encoding said fusion proteins are expressed in step (a) in a cell-free system, and wherein said identifying in step (b) is performed by measuring the function of the fusion proteins.

7. A method for producing a soluble protein domain comprising:
   (a) providing an expression vector which expresses a fusion protein of a first protein with a second protein that is a green fluorescent protein (GFP) or a GFP variant,
   (b) partially digesting said expression vector with DNA decomposing enzyme to obtain two or more DNA fragments of said vector containing deletions of the nucleotide sequence encoding the first protein,
   (c) transforming *E. coli* with each of said DNA fragments prepared in step (b) to obtain two or more transformed *E. coli*,
   (d) isolating a transformed clone of *E. coli* that emits fluorescence among the transformed *E. coli* thus identifying a clone containing DNA that encodes a fusion protein with a soluble protein domain,
   (e) recovering the DNA from the isolated transformed clone,
   (f) synthesizing the soluble protein domain encoded on the recovered DNA in a cell-free system; and
   (g) recovering the soluble protein domain synthesized in step (f).

8. A method for producing a soluble protein domain comprising:
   (a) providing an expression vector comprising a DNA encoding a fusion protein comprised of a first protein and a DNA encoding a second protein which exhibits a function;
   (b) treating said vector with a decomposing enzyme to form two or more digested vectors, each vector comprising a fragment of said DNA encoding the first protein;
   (c) expressing fusion proteins encoded on the digested vectors obtained in step (b);
   (d) identifying the fusion protein exhibiting the function characterizing the functional protein among two or more fusion proteins produced in step (c) as comprising a soluble protein domain of said first protein;

(e) synthesizing the soluble protein domain included in the fusion protein selected in step (d) in a cell-free system; and (f) recovering the soluble protein domain synthesized in step (e).

9. The method of claim 8, wherein the identifying of step (d) is performed by transforming cells with the digested vectors, and selecting a clone of said cells which exhibits said function in the obtained transformants.

10. A method to produce a soluble domain that is a fragment of a starting protein which method comprises (a) synthesizing, in a cell-free system, a protein identified as said soluble domain by:
(i) preparing a multiplicity of fusion proteins, each said fusion protein comprising a functional portion and a fragment of said starting protein,
(ii) assessing each fusion protein for the function of the functional portion; and
(iii) identifying, as a soluble domain, fragments of said protein which are contained in fusion proteins that exhibit the function of the functional portion; and (b) recovering the soluble domain synthesized in step (a).

11. The method of claim 10, wherein said preparing of step (i) is performed in a cell-free system.

12. The method of claim 10, wherein said preparing of step (i) is performed intracellularly.

13. The method of claim 12, wherein said preparing of step (i) is performed in vivo in *E. coli*.

14. The method of claim 10, wherein the functional portion comprises an enzyme, a binding protein, a luminescent protein or a fluorescent protein.

15. The method of claim 14, wherein the fluorescent protein is green fluorescent protein (GFP) or a GFP variant.

16. A method to produce a soluble protein domain that is a fragment of a starting protein which method comprises (a) expressing, in each of at least two *E. coli* colonies, a fusion protein comprising green fluorescent protein (GFP) or a GFP variant fused to different fragments of said starting protein and (b) identifying a transformed *E. coli* colony that emits fluorescence, whereby a colony comprising a fusion protein containing a fragment that is a soluble domain is identified, and (c) producing the soluble protein domain identified in step (b) in a cell-free system; and (d) recovering the soluble protein domain synthesized in step (c).

17. The method of claim 16, wherein each said fragment is obtained by a process comprising digesting nucleic acid encoding a fusion protein comprising said GFP or GFP variant and said starting protein with a DNA digesting enzyme.

18. The method of claim 17, wherein said digesting is either from the 3' or 5' end of the nucleic acid.

* * * * *